(12) United States Patent
Kase et al.

(10) Patent No.: US 6,825,368 B2
(45) Date of Patent: Nov. 30, 2004

(54) METHOD FOR PRODUCING A FATTY ACID

(75) Inventors: Minoru Kase, Kamisu-machi (JP); Keiji Shibata, Kamisu-machi (JP); Eizo Maruyama, Kamisu-machi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/614,833

(22) Filed: Jul. 9, 2003

(65) Prior Publication Data

US 2004/0132147 A1 Jul. 8, 2004

(30) Foreign Application Priority Data

Jul. 15, 2002 (JP) ........................................ 2002-205200

(51) Int. Cl.[7] .............................................. C07C 51/43
(52) U.S. Cl. ........................ 554/211; 554/174; 554/208; 426/330.6; 435/134
(58) Field of Search ................................ 554/174, 208, 554/211; 426/330.6; 435/134

(56) References Cited

U.S. PATENT DOCUMENTS 5,952,518 A * 9/1999 Sugiura et al. ............. 554/208
6,630,189 B2 * 10/2003 Sugiura et al. ............ 426/330.6

FOREIGN PATENT DOCUMENTS

| JP | 11-106782 | 4/1999 |
| WO | WO 99/07812 | 2/1999 |
| WO | WO 01/83655 | 11/2001 |

* cited by examiner

*Primary Examiner*—Deborah D. Carr
(74) *Attorney, Agent, or Firm*—Oblon, Spivak, McClelland, Maier & Neustadt, P.C.

(57) ABSTRACT

The present invention provides a method for producing a saturated fatty acid and an unsaturated fatty acid, which comprises adding and mixing a polyglycerol ester of a fatty acid to a raw fatty acids mixture, cooling the resultant mixture to deposit crystals, and fractionating the saturated fatty acid and the unsaturated fatty acid, wherein a cooling procedure is performed at a cooling rate of 4° C./h or less when a supersaturation ratio is 60% or more and said cooling rate is varied during the cooling, and a glycerides mixture obtained from the fractionated unsaturated fatty acids.

According to the present invention, a saturated fatty acid and an unsaturated fatty acid in a raw fatty acids mixture can be separated easily and efficiently by a dry fractionation process.

20 Claims, No Drawings

METHOD FOR PRODUCING A FATTY ACID

FIELD OF THE INVENTION

The present invention relates to a method for separating a saturated fatty acid and an unsaturated fatty acid from a mixture of fatty acids by a dry fractionation process with a superior efficiency, and use of the separated unsaturated fatty acids.

BACKGROUND OF THE INVENTION

Fatty acids are widely utilized as an intermediate raw material of foods, such as a monoglyceride and a diglyceride, as well as an additive, and an intermediate raw material for other sorts of industrial products. These fatty acids are generally produced by hydrolyzing a vegetable oil such as a rapeseed oil, a soybean oil, or an animal oil such as beef tallow, using a high pressure method, or a decomposition method with an enzyme.

However, fatty acids produced simply by hydrolyzing an animal oil or a vegetable oil as described above, which have natural fatty acid compositions, are not necessarily suitable as a basic raw material for industrial use. In other wards, it is necessary to fractionate unsaturated fatty acids and saturated fatty acids depending on the utilization purpose.

Therefore, it becomes necessary to modify a melting point to obtain a desired mixture of fatty acids. Generally in a fractionation process of fatty acids, a fractionation process using a solvent and a fractionation process using a wetting agent are employed. Although these processes show high efficiencies (e.g. yields) of separation, they pose problems such as an initial cost for facility investment as well as a high running cost for recovery of the solvent or the aqueous solution of the wetting agent and the like. In contrast, a dry fractionation process without using any solvent (e.g. a no solvent process) is an inexpensive fractionation process, and an attempt to solve such problem as low filtration rate, has been made by employing an emulsifier such as a polyglycerol ester of a fatty acid (JP-A-11-106782).

However, even with the dry fractionation process using a polyglycerol ester of a fatty acid, it has become apparent that sufficiently large crystals are not formed under some conditions of cooling rate, retention time or the like, resulting in a low efficiency of filtration.

DISCLOSURE OF THE INVENTION

The present invention provides a method for producing a saturated fatty acid and an unsaturated fatty acid by fractionating the saturated fatty acid and the unsaturated fatty acid by adding and mixing a polyglycerol ester of a fatty acid to a raw fatty acids mixture and cooling them to deposit crystals, wherein a cooling procedure is performed at a cooling rate of 4° C./h or less when an supersaturation ratio is 60% or more, and said cooling rate is varied during the cooling.

In addition, the present invention provides a method for producing a glycerides mixture from the unsaturated fatty acids fractionated by the above method, in which at least 90% by mass of the fatty acid components are unsaturated fatty acids.

DETAILED DESCRIPTION OF THE INVENTION

An object of the present invention is to provide a dry fractionation process for fatty acids using a polyglycerol ester of a fatty acid, enabling to shorten a cycle time and provide an improved efficiency of filtration, quality, and yield by controlling cooling conditions.

Therefore, the present inventor has extensively studied the cooling conditions after adding and dissolving a polyglycerol ester of a fatty acid, and found that when a cooling rate is a specified rate and is varied during the cooling, saturated fatty acids and unsaturated fatty acids can be efficiently fractionated, since a crystal size of saturated fatty acids in a raw fatty acids mixture becomes large and a formation of fine crystals is restrained, resulting in a remarkable improvement in an efficiency of filtration.

Furthermore, the present inventor has found that the method is particularly useful for producing glycerides for foods, because the glycerides mixture produced from the unsaturated fatty acids thus fractionated contains less transform of unsaturated fatty acids and is liquid state free from deposit of crystals at an ordinary temperature, and thus accomplished the above invention.

In the present invention, "a dry fractionation process" means a process to perform solid-liquid separation by cooling a raw fatty acids mixture while stirring if necessary, without using water in an amount such as to allow a phase separation and without using any solvent, and separating a solid component deposited thereby using a separation system such as filtration, centrifugation and sedimentation. "A composition of fatty acids" means the composition of the total amount of fatty acids derived from free fatty acids and the fatty acid residue in glyceride. A composition of fatty acid can be measured by gas chromatography. "A ratio of saturated fatty acids" means the ratio of saturated fatty acids ($C_{12}$ to $C_{22}$) in such composition of fatty acids. "A clear melting point" means a value as measured according to Standard Methods for the Analysis of Fats, Oils and Related Materials (Japan Oil Chemists' Society) (2.2.4.1-1996).

In the present invention, a raw fatty acids mixture to be fractionated to saturated fatty acids and unsaturated fatty acids is produced by hydrolyzing a vegetable oil such as a rapeseed oil and a soybean oil, or an animal oil such as beef tallow, by a steam decomposition method, by utilizing lipase as a catalyst or the like. In this connection, fatty acids include a monoglyceride, a diglyceride and a triglyceride in addition to fatty acids. Further, unsaturated fatty acids include some amount of saturated fatty acids, and saturated fatty acids include unsaturated fatty acids. Still further, glycerides include some amount of fatty acids in addition to the above monoglyceride, diglyceride and triglyceride. The method according to the present invention is effective when an amount of fatty acids in a raw fatty acids mixture is preferably at least 50% by mass, particularly at least 85% by mass, and the above glycerides may be present therein. Furthermore, as a raw fatty acids mixture, those having a ratio of saturated fatty acids ($C_{12}$ to $C_{22}$) such as palmitic acid and stearic acid in the fatty acid components in an amount of 5 to 60% by mass, particularly 8 to 50% by mass, are preferred. For instance, fatty acids originated from a vegetable oil such as a soybean oil and a sunflower oil can be employed.

Origin of a polyglycerol ester of a fatty acid to be used in the present invention is not limited. The ester may be any of those obtained by esterification of fatty acids and a polyglycerol of natural origin, and those obtained by esterification of fatty acids and a synthetic polyglycerol produced by polymerization of glycidol, epichlorohydrine or the like. An average degree of polymerization of the polyglycerol in the polyglycerol ester of fatty acids is preferably at least 3, particularly at least 4, from the viewpoint of obtaining a crystal state easy for filtration. Further, the fatty acids to be reacted with a polyglycerol are preferably composed of saturated or unsaturated fatty acids having carbon atoms of 10 to 22, particularly 12 to 18, from the viewpoint of obtaining a crystal state easy for filtration. Said fatty acids may be composed of a single fatty acid, but are preferably composed of a mixture of fatty acids from the viewpoint to obtain a crystal state easy for filtration. An esterification reaction between the polyglycerol and the fatty acids may be performed by any of methods such as a method in which a mixture of these substances is added with an alkaline catalyst such as sodium hydroxide, then directly esterified in an inert gas stream such as nitrogen at 200 to 260° C., and a method in which an enzyme is used.

The above-described polyglycerol ester of a fatty acid may be used in combination of two or more kinds, and an amount thereof to be added is preferably around 0.001 to 5% by mass, more preferably around 0.05 to 1% by mass, based on the raw fatty acids mixture.

According to the present invention, as described above, saturated fatty acids and unsaturated fatty acids are efficiently produced, by adding and mixing a polyglycerol ester of a fatty acid as an additive to a raw fatty acids mixture, cooling them to deposit crystals, and fractionating to a liquid portion and a crystal portion. In this connection, the liquid portion is unsaturated fatty acids and the crystal portion is saturated fatty acids. Said polyglycerol ester of a fatty acid is preferably mixed with the raw fatty acids mixture and dissolved therein at a temperature higher than the clear melting point thereof so as to be completely dissolved in the raw fatty acids mixture.

It is necessary that a cooling procedure is performed at a cooling rate of 4° C./h or less when a supersaturation ratio is 60% or more and the cooling rate is varied during the cooling. The supersaturation ratio is a value as calculated using the formula (1), and represents a concentration (abbreviated to C) at a certain temperature (abbreviated to t) so as to range from 0 to 100% within a metastable zone.

$$\text{Supersaturation ratio} = \frac{C_{(t)} - Cs_{(t)}}{Cu_{(t)} - Cs_{(t)}} \times 100 \ (\%) \quad (1)$$

Definitions of solubility (abbreviated to Cs), supersolubility (abbreviated to Cu) and metastable zone are described in page 434 of "Kagakukougaku Binran, 5th revised edition" (published by MARUZEN CO., LTD). In the present invention, in formula (1), "concentration" means a ratio of saturated fatty acids ($C_{12}$ to $C_{22}$) in the liquid portion. A supersaturation ratio becomes 100% when a concentration (abbreviated to C) is equal to a supersolubility (abbreviated to Cu) at a certain temperature (abbreviated to t), and the supersaturation ratio becomes 0% when a concentration is equal to a solubility (abbreviated to Cs).

Here, when a solution and a free solute coexist in an equilibrium, the solution is called as a saturated solution and a concentration of the solute in the solution is called as a solubility. A curve showing a relation between solubility and temperature is called as a solubility curve.

In addition, the supersolubility is explained as follows. When a solution in an unsaturated zone is slowly cooled, crystals do not deposit at a temperature at which a concentration equal to a solubility, but deposit when the cooling is further continued to some extent. Temperatures at which crystals starts to deposit are measured for various solutions having different concentrations. A relation between the temperatures and the concentrations is called as a supersolubility. A curve showing the relation between temperature and concentration is called as a supersolubility curve.

A metastable zone means a zone enclosed by the supersolubility curve and the solubility curve.

Crystallization can be proceeded in a short time by cooling rapidly and set a supersaturation ratio so as to become 100%, but too rapid cooling tends to lower an efficiency of filtration because crystals become fine due to an insufficient crystal growth. Contrary, when a supersaturation ratio is 0%, crystals do not deposit. In the cooling procedure of the present invention, it is necessary to control a cooling rate at 4° C./h or less when a supersaturation ratio is 60% or more, from the viewpoints of forming large crystals providing a high efficiency of filtration, restraining formation of fine crystals, and obtaining an improved quality and yield. Furthermore, by varying a cooling rate during the cooling, cycle time can be shortened and crystals with better filterability can grow efficiently by restraining formation of fine crystals, compared with a cooling at a constant rate. An average particle diameter of crystals is preferably at least 100 μm, more preferably at least 200 μm.

Cooling rate is preferably varied at least once, more preferably 2 to 4 times. The cooling rate is preferably high at the initial stage of cooling, reduced when a supersaturation ratio becomes 60% or more, then raised again when the supersaturation ratio becomes below 60%. More preferably, the cooling rate is 5 to 20° C. at the initial stage of cooling, reduced to 4° C./h or less when a supersaturation ratio becomes 60% or more (more preferably 70 to 95%), then set to 1 to 10° C./h if necessary when a supersaturation ratio becomes below 60% (more preferably 30 to 55%). The cooling rate may be adjusted so as to vary smoothly immediately before and after the change of cooling rate.

The final temperature of cooling depends on a kind of a raw fatty acids mixture and a required quality of the product. For instance, when a soybean fatty acids mixture is used as a raw material, the final temperature is preferably −5 to 0° C. Further, a solution is preferably agitated during the cooling in order to form large crystals with a high efficiency of filtration and restrain formation of fine crystals. More preferably, a solution is agitated at an agitation speed of 10 to 200 rpm.

As a separation method for the crystals formed, any system such as filtration, centrifugation and sedimentation can be applied, and any of a batch process and a continuous process may also be employed.

By using the solid-liquid separation according to the present invention, saturated fatty acids can be separated as a solid portion more efficiently and an effective components such as vitamin E present in a raw oil can be localized in a liquid portion.

A liquid portion obtained by the solid-liquid separation is unsaturated fatty acids. Therefore, a glycerides mixture which contains unsaturated fatty acids in a ratio of at least 90% by mass of the total fatty acid components can be obtained efficiently by reacting unsaturated fatty acids thus obtained with a glycerol in the presence of lipase.

Said reaction of unsaturated fatty acids mixture and a glycerol is preferably performed using an immobilized lipase. Here, if a lipase with a high regioselectivity is used, a glycerides mixture, which contains at least 50% by mass of diglyceride containing unsaturated fatty acids in a ratio of at least 90% by mass of the total fatty acid components, can be obtained. Among such glycerides containing a high ratio of diglyceride, those containing 50 to 100% by mass of diglyceride are preferable, and those containing 70 to 100% by mass of diglyceride are more preferable. On the other hand, if a lipase with a low regioselectivity is used, a glycerides mixture, which contains a triglyceride as a main component containing unsaturated fatty acids in a ratio of at least 90% by mass of the total fatty acid components, can be obtained.

Lipase may be used in a free state, but is preferably used in an immobilized state on an ion exchange resin, particularly on an anion exchange resin. The above-described reaction of unsaturated fatty acids mixture and glycerol is preferably performed while removing water formed by the reaction from the system by means such as vacuum dehydration, inert gas purging and use of a water absorbing agent in order to obtain an improved yield of the esterification. Details of these reactions are described, for instance, in JP-A-57-8787 and JP-A-1-71495.

EXAMPLES
[Method for Measuring Supersaturation Ratio]

First, a raw material to be fractionated was added with a polyglycerol ester of a fatty acid and stirred at a certain constant temperature for at least 72 hours. The mixture was filtered and a ratio of saturated fatty acids in a liquid portion was measured. This procedure was repeated several times at various temperatures. The ratio of saturated fatty acids thus obtained were plotted against the temperatures to obtain a solubility curve [Cs(t)].

Next, each sample collected from each liquid portion described above was cooled while stirring at a constant cooling rate (0.02° C./min) to determine a temperature at which fine crystals started to deposit. This procedure was repeated for the samples having different ratio of saturated fatty acids. The ratio of saturated fatty acids were plotted against the temperatures at which fine crystals started to deposit to obtain a supersolubility curve [Cu(t)].

Furthermore, a ratio of saturated fatty acids in the liquid portion was determined at a certain temperature during cooling and designated as C(t).

A supersaturation ratio at a temperature t° C. was calculated from these results according to the formula (1).

Example 1
[Preparation of a Raw Fatty Acids Mixture 1]

Soybean oil was hydrolyzed by a conventional method (a high pressure decomposition method) to prepare a raw fatty acids mixture. A composition of fatty acids, a ratio of saturated fatty acids and a concentration of fatty acids in the fatty acids mixture used are shown in Table 1.

[Fractionation of Fatty acids 1]

To 1,000 g of the fatty acids mixture prepared above, a 2 g of a mixture of polyglycerol esters of fatty acids (decaglycerol ester) shown in Table 2 was added and homogeneously dissolved at 80° C. Then, the mixture was cooled under the conditions shown in Table 3 while stirring at 50 rpm. A supersaturation ratio at a temperature range from 20° C. to 15° C. during the cooling was 60% or more. Subsequently, using a filter cloth made of nylon, such as NY1260NLK (trade name, manufactured by Mitsubishi Kakoki Kaisha, Ltd.) (filtration area: 39 cm$^2$), the solution was filtrated under a pressure of 0.03 MPa, and fractionated to a liquid portion (unsaturated fatty acids) and a solid portion (a crystal portion; saturated fatty acids). A filtration time required to obtain 500 ml of filtrate, a melting point of the liquid portion, a yield of the liquid portion, and a ratio of fatty acids ($C_{12}$ to $C_{22}$) in each of the liquid portion and the solid portion were measured. Results are shown in Table 4.

TABLE 2

Physical properties of polyglycerol esters of fatty acids

| PGE No. | Polyglycerol ester of fatty acid (additive) | | | | | | | | AV [mg-KOH/g] | OHV | Clear m.p. [° C.] |
|---|---|---|---|---|---|---|---|---|---|---|---|
| | Fatty acid composition [% by mass] | | | | | | | | | | |
| | 12 | 14 | 16 | 18 | 18:1 | 18:2 | 20 | 22 | | | |
| PGE 1 | 20 | 5 | 25 | 30 | 20 | 0 | 0 | 0 | 6 | 48 | 37 |

TABLE 1

Analysis of raw fatty acids mixture

| Ratio of saturated fatty acids ($C_{12-22}$) | Composition of fatty acids [% by mass] | | | | | | | | | | | Conc'n of fatty acids |
|---|---|---|---|---|---|---|---|---|---|---|---|---|
| [% by mass] | 12 | 14 | 16 | 18 | 18:1 | 18:2 | 18:3 | 20 | 20:1 | 22 | 22:1 | [% by mass] |
| 15 | 0 | 0 | 10 | 4 | 23 | 54 | 8 | 1 | 0 | 0 | 0 | 92 |

TABLE 3

Fractionation conditions

| Fractionation condition No. | Temp. range Cooling rate | Temp. range Cooling rate | Temp. range Cooling rate | Final temp. Retention time | Cooling time |
|---|---|---|---|---|---|
| 1 | 80→20 [° C.] 10 [° C./h] | 20→−3 [° C.] 4 [° C./h] | | −3 [° C.] 1 [h] | 12.8 [h] |

TABLE 3-continued

| | Fractionation conditions | | | | |
|---|---|---|---|---|---|
| Fractionation condition No. | Temp. range Cooling rate | Temp. range Cooling rate | Temp. range Cooling rate | Final temp. Retention time | Cooling time |
| 2 | 80→20 [° C.] 10 [° C./h] | 20→15 [° C.] 2 [° C./h] | 15→-3 [° C.] 4 [° C./h] | -3 [° C.] 1 [h] | 14.0 [h] |
| 3 | 80→20 [° C.] 10 [° C./h] | 20→15 [° C.] 4 [° C./h] | 15→-3 [° C.] 6 [° C./h] | -3 [° C.] 1 [h] | 11.3 [h] |
| 4 | 80→15 [° C.] 10 [° C./h] | 15→-3 [° C.] 4 [° C./h] | | -3 [° C.] 1 [h] | 12.0 [h] |
| 5 | 80→-3 [° C.] 10 [° C./h] | | | -3 [° C.] 1 [h] | 9.3 [h] |
| 6 | 80→-3 [° C.] 10 [° C./h] | | | -3 [° C.] 1 [h] | 28.7 [h] |

TABLE 4

| | Results of fractionation | | | | |
|---|---|---|---|---|---|
| | | Liquid portion | | | Solid portion |
| Fractionation Condition No. | Filtration time [min] | Ratio of sat'd fatty acids ($C_{12-22}$) [% by mass] | Clear m.p. [° C.] | Yield [% by mass] | Ratio of sat'd fatty acids ($C_{12-22}$) [% by mass] |
| 1 | 1 | 4 | -1 | 78 | 56 |
| 2 | 1 | 4 | -1 | 79 | 57 |
| 3 | 2 | 4 | -1 | 78 | 54 |
| 4 | 60 or more | — | — | 3 | — |
| 5 | 60 or more | — | — | 2 | — |
| 6 | 2 | 4 | -1 | 74 | 55 |

As apparent from Table 3 and Table 4, the following can be understood. Namely, when cooling is performed under the conditions where an supersaturation ratio is 60% or more and a cooling rate is 4° C./h or less and varied during the cooling, saturated fatty acids and unsaturated fatty acids can be efficiently separated by a dry fractionation process, since large crystals of saturated fatty acids grow in a short time restraining formation of fine crystals. In contrast, a cooling procedure at a too high rate is not preferable due to a decreased efficiency of filtration, and a cooling procedure at a too low rate is also not preferable due to an extended cycle time resulting in a higher cost. Thus, it is preferable to set the conditions so as to complete the cooling within 20 hours.

Next, results of production of a glycerides mixture using a fatty acids mixture produced by the method of the present invention will be described hereinbelow.

[Preparation of a Raw Fatty Acids Mixture 2 (Enzyme Method)]

A mixture of 5,000 g of a soybean oil, 3,000 g of distilled water and 500 g of an immobilized enzyme obtained by immobilizing lipase AY (Amano Enzyme Co., Ltd.) on an anion exchange resin (Duolite A-568: ROHM & HASS Corp.) was reacted at 40° C. for 15 hours while stirring under a nitrogen atmosphere. The immobilized enzyme was then removed by filtration and the sweet water was removed after leaving for standing. Subsequently, 50% by mass of distilled water heated to 70° C. based on the reacted oil was added to the oil and stirred well under a nitrogen atmosphere, and then an aqueous phase was removed after leaving for standing. This procedure was repeated twice followed by a vacuum dehydration at 70° C. to prepare a raw fatty acids mixture. A composition of the decomposed fatty acids is shown in Table 5.

[Fractionation of Fatty Acids 2]

A 3,000 g of the fatty acids thus obtained was heated to 80° C. and added with 6 g of the polyglycerol ester of fatty acids shown in Table 2 to obtain a homogeneous solution by heating at 80° C. for 15 minutes. The solution was then cooled while stirring at 50 rpm, under the fractionation condition No. 2 shown in Table 3. Subsequently, the solution was divided into three portions, each of which was filtrated under a pressure of 0.03 MPa, using a filter cloth [made of nylon, NY1260NLK (trade name, manufactured by Mitsubishi Kakoki Kaisha, Ltd.)] (filtration area: 39 cm$^2$). Results of analysis on a composition of fractionated fatty acids are shown in Table 5.

Example 2
[Production of Diglycerides Mixture 1]

A mixture of 868 g of a liquid portion of the fractionated fatty acids obtained in the above [Fractionation of fatty acids 2], 132 g of glycerol and 50 g of an immobilized lipase (Lipozyme RM IM; Novozymes A/S) was reacted at 50° C. for 2.5 hours under a reduced pressure. After the reaction, the immobilized lipase was separated from the reaction liquid by filtration. The reacted oil thus obtained was subjected to molecular distillation at 230° C. and 0.05 mmHg to remove fatty acids and monoglycerides. The distilled oil obtained was acid-treated by adding 2% by mass of a 10% aqueous solution of citric acid and stirring at 70° C. for 30 minutes under a nitrogen atmosphere followed by vacuum dehydration at 70° C. The acid-treated oil thus obtained was then washed by adding 50% by mass of distilled water heated to 70° C. based on the acid-treated oil, and stirred well under a nitrogen atmosphere followed by separating an aqueous phase after leaving for standing. This procedure was repeated twice. The washed oil obtained was then subjected to steam deodorization at 230° C. for 60 minutes under a reduced pressure to obtain a diglycerides mixture containing less saturated fatty acids and less trans-acids. Results of analysis on a composition of fatty acids in the diglycerides mixture are shown in Table 5.

Example 3
[Production of Triglycerides Mixture 1]

A mixture of 868 g of a liquid portion of the fractionated fatty acids obtained in the above [Fractionation of fatty acids 2], 60 g of glycerol and 50 g of an immobilized lipase obtained by immobilizing lipase AY (Amano Enzyme Co., Ltd.) on an anion exchange resin (Duolite A-568: ROHM & HASS Corp.) was reacted at 40° C. for 8 hours under a reduced pressure. After the reaction, the immobilized lipase was separated from the reaction liquid by filtration. The reacted oil thus obtained was subjected to molecular distillation at 230° C. and 0.05 mmHg to remove fatty acids and monoglycerides. The resultant distilled oil was then subjected to steam deodorization at 230° C. for 60 minutes under a reduced pressure to obtain a triglycerides mixture containing less saturated fatty acids and less trans-acids. Results of analysis on a composition of fatty acids in the triglycerides mixture are shown in Table 5.

Comparative Example 1

Furthermore, results of production of a glycerides mixture produced from fatty acids produced by a distillation method will be described.
[Fractionation of Fatty Acids 3 (Distillation Method)]

A 3,000 g of the fatty acids obtained by [Preparation of raw fatty acids mixture 2] in Example 1 was distilled at 200° C. for 120 minutes under a reduced pressure of 5 mmHg to remove palmitic acid. Results of analysis on a composition of the distilled fatty acids mixture are shown in table 5.
[Production of Diglycerides Mixture 2]

A mixture of 868 g of the distilled fatty acids obtained, 132 g of glycerol and 50 g of an immobilized lipase (Lipozyme RM IM; Novozymes A/S) was reacted at 50° C. for 2.5 hours under a reduced pressure. After the reaction, the immobilized lipase was separated from the reaction liquid by filtration. The reacted oil thus obtained was subjected to molecular distillation at 23° C. and 0.05 mmHg to remove fatty acids and monoglycerides. The distilled oil obtained was acid-treated by adding 2% by mass of a 10% aqueous solution of citric acid and stirring at 70° C. for 30 minutes under a nitrogen atmosphere followed by vacuum dehydration at 70° C. The acid-treated oil thus obtained was then washed by adding 50% by mass of distilled water heated to 70° C. based on the acid-treated oil and stirred well under a nitrogen atmosphere, followed by separating an aqueous phase after leaving for standing. This procedure was repeated twice. The resultant washed oil was then subjected to steam deodorization at 230° C. for 60 minutes under a reduced pressure to obtain a diglycerides mixture. Results of analysis on a composition of fatty acids in the diglycerides mixture are shown in Table 5.

Comparative Example 2
[Production of Triglycerides Mixture 2]

A mixture of 868 g of the distilled fatty acids obtained in Comparative Example 1, 60 g of glycerol and 50 g of an immobilized lipase obtained by immobilizing lipase AY (Amano Enzyme Co., Ltd.) on an anion exchange resin (Duolite A-568: ROHM & HASS Corp.) was reacted at 40° C. for 8 hours under a reduced pressure. After the reaction, the immobilized lipase was separated from the reaction liquid by filtration. The reacted oil thus obtained was subjected to molecular distillation at 230° C. and 0.05 mmHg to remove fatty acids and monoglycerides. The resultant distilled oil was then subjected to steam deodorization at 230° C. for 60 minutes under a reduced pressure to obtain a triglycerides mixture. Results of analysis on a composition of fatty acids in the triglycerides mixture are shown in Table 5.

TABLE 5

| | Ratio of sat'd fatty acids ($C_{12-22}$) [% by mass] | Trans-acid [% by mass] |
|---|---|---|
| Raw fatty acids mixture (Enzymatic method) Fractionated fatty acids | 15 | 0.6 |
| Liquid portion | 3 | 0.6 |
| Solid portion | 56 | 0.2 |
| Distillated fatty acids | 6 | 3.3 |
| Example 2 (diglycerides) | 3 | 2.9 |
| Example 3 (triglycerides) | 3 | 3.0 |
| Comp. Example (diglycerides) | 6 | 5.8 |
| Comp. Example (triglycerides) | 6 | 6.0 |

As apparent from Table 5, it can be understood that in a production of a glycerides mixture from fatty acids and glycerol, use of the unsaturated fatty acids produced by the method of the present invention gives a glycerides mixture containing less trans-acids and less saturated fatty acids compared with that in the case using the fatty acids produced by a distillation method.

INDUSTRIAL APPLICABILITY

According to the present invention, saturated fatty acids and unsaturated fatty acids in a raw fatty acids mixture can be easily and efficiently separated by a dry fractionation. In addition, use of the unsaturated fatty acids thus fractionated can provide a liquid glycerides mixture containing less trans-form of unsaturated fatty acids at a low cost.

What is claimed is:

1. A method of performing solid-liquid separation of a fatty acids mixture comprising:
   i) adding a polyglycerol ester of a fatty acid to a fatty acids mixture;
   ii) cooling a resultant mixture at a cooling rate to deposit crystals of a saturated fatty acid; and
   iii) fractionating said crystals of a saturated fatty acid from a portion comprising an unsaturated fatty acid,
   wherein said cooling rate is 4° C./h or less when a supersaturation ratio is 60% or more; and
   wherein said cooling rate is adjusted at least once during cooling.
2. The method of claim 1, wherein said cooling rate is reduced when a supersaturation ratio becomes 60% or more.
3. The method of claim 1, wherein cooling is performed while stirring.
4. The method of claim 2, wherein cooling is performed while stirring.
5. The method of claim 1, wherein said fatty acids mixture is a hydrolyzed vegetable oil or a hydrolyzed animal oil.
6. The method of claim 1, wherein said fatty acids mixture comprises at least 50% by mass of fatty acids.
7. The method of claim 1, wherein said fatty acids mixture has a ratio of saturated fatty acids in an amount of 5 to 60% by mass.

8. The method of claim 1, wherein said polyglycerol ester of a fatty acid has an average degree of polymerization of at least 3.

9. The method of claim 1, wherein a fatty acid component of said polyglycerol ester of a fatty acid has 10 to 22 carbon atoms.

10. The method of claim 1, wherein a fatty acid component of said polyglycerol ester of a fatty acid is comprised of a mixture of fatty acids.

11. The method of claim 1, wherein said polyglycerol ester of a fatty acid is used in amount of 0.001 to 5% by mass based on said fatty acids mixture.

12. The method of claim 1, wherein said polyglycerol ester of a fatty acid is completely dissolved in said fatty acids mixture prior to cooling.

13. The method of claim 1, wherein said cooling rate is adjusted 2 to 4 times.

14. The method of claim 1, wherein said cooling rate is 5 to 20° C. at an initial stage of cooling;

reduced to 4° C./h when a supersaturation ratio becomes 60% or more; and set to 1 to 10° C./h when a supersaturation ratio becomes below 60%.

15. The method of claim 1, wherein said crystals of a saturated fatty acid have an average particle diameter of at least 100 µm.

16. The method of claim 1, wherein said crystals of a saturated fatty acid have an average particle diameter of at least 200 µm.

17. A method of producing a glyceride comprising:

i) adding a polyglycerol ester of a fatty acid to a fatty acids mixture;

ii) cooling a resultant mixture at a cooling rate to deposit crystals of a saturated fatty acid; and iii) fractionating said crystals of a saturated fatty acid from a portion comprising an unsaturated fatty acid, wherein said cooling rate is 4° C./h or less when a supersaturation ratio is 60% or more; and wherein said cooling rate is adjusted at least once during cooling; and iv) reacting said unsaturated fatty acid with glycerol in the presence of lipase.

18. The method of claim 17 wherein said cooling rate is reduced when a supersaturation ratio becomes 60% or more.

19. The method of claim 1, wherein cooling is performed while stirring.

20. The method of claim 19, wherein said cooling rate is reduced when a supersaturation ratio becomes 60% or more.

* * * * *